Figure 1:
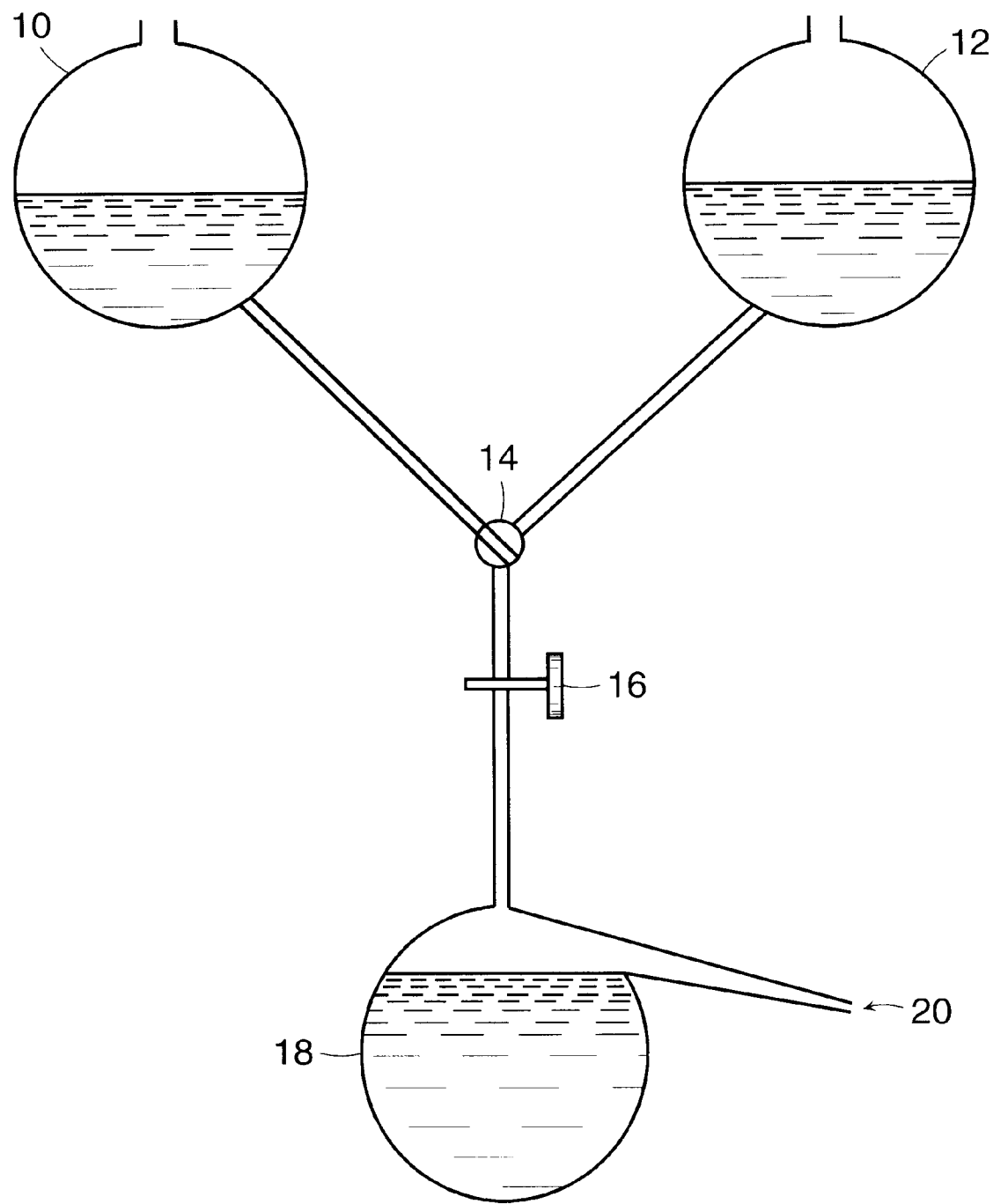

United States Patent [19]
Disney

[11] Patent Number: 5,948,633
[45] Date of Patent: Sep. 7, 1999

[54] METHOD FOR DETERMINING THE EFFECT OF A CHEMICAL COMPOUND ON MICROORGANISMS GROWING IN CONTINOUS CULTURE

[76] Inventor: Loren Disney, P.O. Box 656, Boston, Mass. 02130

[21] Appl. No.: 08/908,493

[22] Filed: Aug. 7, 1997

[51] Int. Cl.⁶ ..................................................... C12Q 1/18
[52] U.S. Cl. .......................... 435/32; 435/287.1; 435/813
[58] Field of Search ................................ 435/30, 32, 39, 435/288.5, 287.1, 288.1, 288.7, 289.1, 304.1, 813

[56] References Cited

U.S. PATENT DOCUMENTS

| | | | |
|---|---|---|---|
| 2,990,339 | 6/1961 | Frank et al. | 435/288.7 |
| 5,057,432 | 10/1991 | Wangersky et al. | 435/289 |
| 5,563,043 | 10/1996 | Schalkowsky et al. | 435/32 |

OTHER PUBLICATIONS

Sterkenburg et al. 'Phenotypic variability of the sensitivity of cycloserine of *Klebsiella aerogenes* NCTC 418, growing in chemostat culture'. J. Gen. Microbiology. vol. 124 (1981), pp. 29–34.

Tuomanen et al. 'The rate of killing of *Escherichia coli* by beta–lactam antibiotics is strictly proportional to the rate of bacterial growth'. J. Gen. Microbiology. vol. 132 (1986), pp. 1297–1304.

Berg eta l. 'Effect of antecedent growth conditions on sensitivity of *Escherichia coli* to chlorine dioxide.' Appl. Environ. Microbiol. vol 44 (1982), pp. 814–819.

Bradshaw et al. 'The effects of triclosan and zinc citrate, alone and in combination, on a community of oral bacteria grown in vitro.' J. Dent. Res. vol. 72 (1993), pp. 25–30.

Cozens et al. 'Evaluation of the bactericidal acitivity of beta–lactam antibiotics on slowly growing bacteria cultured in the chemostat'. Antimicrob. Agents Chemother. vol. 29 (1986), pp. 797–802.

Gilbert et al. 'Influence of growth rate and nutrient limitation on the gross cellular composition of *Pseudomonas aeruginosa* and its resistance to 3–and 4–chlorophenol'. J. Bacteriology. vol. 133 (Mar. 1978), pp. 1066–1172.

Johnson et al. 'Factors influencing the susceptibility of *Candida albicans* to the polyenoic antibiotics nystatin and amphotericin B'. J. Gen. Microbiology. vol. 104 (1978), pp. 325–333.

Koch et al. 'Growth conditions and rifampin susceptibility'. Antimicrob. Agents and Chemother. vol. 15 (Feb. 1979), pp. 220–228.

Dissertation Abstracts International. vol. 43 (1982), p. 87. Abstract No. 82:3843 of Longstreth. 'Interaction of aminoglycoside pharmacokinetics and bacterial population kinetics in a chemostat'.

Millar et al. 'Bactericidal activity of antimicrobial agents slowly growing *Helicobacter pylori*'.Anitmicrob. Agents Chemother. vol. 36 (1992), pp. 185–187.

*Primary Examiner*—William H. Beisner

[57] ABSTRACT

A device and process for determining the effect of an antimicrobial agent or other compound on a microorganism growing in continous broth culture. The microorganisms are grown in a vessel of fixed volume (18), which is supplied with a constant inflow of nutrient broth selected from one of two resevoirs. The culture is first stabilized by drawing broth from resevoir (10), which contains nutrient broth only, and then at a particular time the inflow is switched to resevoir (12), which contains nutrient broth and the compound to be tested. By measuring the density of the culture, in particular by counting the organisms as they leave the drain (20), the growth rate of the microorganisms can be calculated as a function of time or compound concentration.

1 Claim, 1 Drawing Sheet

METHOD FOR DETERMINING THE EFFECT OF A CHEMICAL COMPOUND ON MICROORGANISMS GROWING IN CONTINOUS CULTURE

BACKGROUND

1. Field of Invention

This invention provides a method for determining the effect of a chemical compound on a given microorganism, subsequently called the analytic chemostat method.

2. Description of Prior Art

Determining the effect of chemical compounds on microbial cultures is of importance both in clinical applications end in assessing new compounds for antimicrobial activity. Although a number of assays have been developed for this purpose none has achieved a high degree of precision and reproducibility This may be because all the methods currently in use involve inoculating the organism to be tested into a fixed quantity of media, solid or liquid. Organisms growing in this manner undergo a succession of physiological states caused by the depletion of nutrients and the build up of toxic metabolites. Indeed, cultures grown on limited media will eventually stop growing independently of the action of the introduced compound. The effect of the antimicrobial agent is therefore combined with a number of naturally occuring inhibitory factors, complicating interpretation of the results.

In order to determine the effect of an antimicrobial agent on microorganisms growing in culture it is necessary to have some method of measuring growth or metabolic activity and to measure growth in the presence, and in the absence, of the compound tested. If the cultures are to be grown on limited media two cultures are required, with growth in the absence of the antimicrobial agent serving as the control experiment. Growth is traditionally determined by visually inspecting the media for colonies, in the case of solid media, or opacity in liquid media, after a period of incubation. This is essentially an "all or nothing" approach and organisms are regarded as sensitive, or resistant, to a particular concentration of an antimicrobial compound. To achieve greater precision several cultures are inoculated simultaneously, with the concentration of antimicrobial agent varied by a series of dilutions. Using these methods the minimum concentration needed to inhibit growth, or MIC, can be determined within approximately a factor of two. The advent of more sophisticated methods of measuring growth has done little to improve on these results.

OBJECTS AND ADVANTAGES

Accordingly, the objects and advantages of the analytic chemostat and the methods of its use as described in my above patent can be summarized as follows:

(a) to provide a method of determining the effect of antimicrobial agents on microorganisms that is more precise than those currently in use;

(b) to provide a method of determining growth rate as a function of antimicrobial concentration in a single experiment; and (c) to provide a method of studying the physiological effect of an antimicrobial agent by varying the limiting nutrient in the chemostat.

DRAWING FIGURE

The FIGURE shows a simple embodiment of the invention.

REFERENCE NUMERALS IN DRAWINGS 10 resevoir containing nutrient broth 12 resevoir containing nutrient broth and antimicrobial agent 14 two position valve selecting between resevoir 10 and resevoir 12

16 stopcock 18 growth vessel 20 drain

DESCRIPTION

The FIGURE shows a simple embodiment of the invented method. It represents both an actual device and a schematic expression of the method itself. Two resevoirs 10 and 12 are connected to a selection valve 14 by tubing which then passes through stopcock 16 into growth vessel 18. This arrangement allows a choice of nutrient broth (contained in 10) or nutrient broth plus antimicrobial agent (contained in 12) to be added to growth vessel 18 at a constant rate (controlled by stopcock 16). The contents of the growth vessel are maintained at constant volume by drain 20.

OPERATION

The chemostat is a device by which microbes are maintained in stable broth culture by continously adding nutrient media to a vessel equipped with an overflow drain. It is presently used to maintain stock cultures and study ecological and adaptive properties of microorganisms.

The essential feature of the method described here is to use the chemostat as an analytic instrument by utilizing the fact that the rate of organisms leaving the vessel is related to the density of organisms in the culture and to the growth rate of the culture. By counting the organisms leaving the vessel it is therefore possible to measure growth rate directly.

The method can be illustrated by reference to the simple embodiment shown in the FIGURE. Suppose that initially valve 14 is adjusted such that nutrient broth flows into the growth vessel from resevoir 10 at a constant rate. Eventually a steady state is established in which the number of organisms leaving the growth vessel via drain 20 is equal to the number created by cell division in a given unit of time (in general some essential nutrient in the broth is present in limiting quantity). The rate at which organisms leave via drain 20 is related to the number present in the growth vessel by the following formula:

$$z = x * f/v \tag{1}$$

where $x$ = number of microbes in the growth vessel $f$ = flow rate $v$ = volume of growth vessel $z$ = rate of microbes leaving the growth vessel Now suppose that valve 14 is switched from resevoir 10 to resevoir 12 at time $t_o$ and that resevoir 12 contains antimicrobial agent S at concentration $s_o$. The concentration of S in the growth vessel at time t will then be given by the formula $$s = s_o(1 - e^{-f*t/v}). \tag{2}$$

The number of microbes in the growth vessel will be increased by cell division and decreased via drain 20 by a rate proportional to the number of microbes in the vessel. At some point cell division will cease as all the organisms present will have been killed or rendered non viable. At this time the concentration of S in the growth vessel (given by s in the above formula) will correspond to the minimum inhibitory concentration (MIC), a well known index of antimicrobial effect. It would therefore be of use to determine this value from the available data. This can be done by measuring the rate at which organisms leave the vessel, either by counting samples under a microscope or by using an automated cell counting device. This value corresponds to z in formula (1). At the point that the MIC has been reached cell division will have ceased and the value of z will begin to decrease by simple exponential decay. This can be expressed mathematically by equation (3)

$$z = z_{mic} \, e^{-f^* t/v} \qquad (3)$$

where $z_{mic}$ is the rate that organisms are leaving the vessel at the time that the level of antimicrobial agent in the growth vessel reaches the MIC. Since f and v are constants the graph of z vs t on semilogarithmic paper will be a straight line with slope $-f/v$ when equation (3) is satisfied. The earliest time at which this condition applies, $t_{mic}$, can be read from the graph. By inserting this value in equation (2) we get the desired result:

$$MIC = S_o (1 - e^{-f^* t_{mic}/V}) \qquad (4)$$

SUMMARY, RAMIFICATIONS, AND SCOPE

Accordingly, the reader will see that the analytic chemostat provides a method of calculating the MIC of an antimicrobial agent in a single experiment with a precision previously unatainable. However, the usefullness of the device is not limited to this single application; a number of alternate applications and embodiements are listed below as examples.

By subtracting the exponential decay factor from the rate of change of the number of organisms in the growth vessel it is possible to calculate an instantaneous value for the growth rate of the culture. This value can be graphed as a function of time or antimicrobial concentration. In this embodiment the MIC corresponds to a growth rate of zero.

The physiological effect of the antimicrobial agent on the microbial cell can be studied by varying the limiting nutrient in the broth.

The above calculations and graphs can be performed automatically in a computer. In a preferred embodiment nutrient broth can be pumped into the growth vessel by a peristaltic pump or similar device, the drain can be attached to a flow cytometer or other automated counting device and the data processed as it is generated.

Thus the scope of the invention should be determined by the appended claims and their legal equivalents, rather than by the examples given.

I claim:

1. A method for determining the effect of a chemical compound on a given microorganism comprising:

(a) conducting an experiment whereby at time to a reservoir containing a compound at concentration S is attached to an inlet of a chemostat device previously fitted with a means for determining cell density of said microorganism as a function of time, said means counting cells of said microorganism and recording the time the cells pass through an outlet drain of the chemostat device, (b) determining the function describing the derivative of the cell density as a function of time obtained in step (a) by methods of numerical analysis, (c) determining cell growth rate by subtracting from the derivative determined in step (b) the exponential decay function $$D(e^{-f^* t/v})$$

where D is the density of cells at time t, f is the flow rate, and v is the reaction volume of the chemostat device, (d) determining the concentration of the compound in the chemostat device as a function of time by direct measurement or by applying the formula $$S = S_o (1 - e^{-f^* t/v})$$

where $S_o$ is the concentration of the compound in the reservoir, S is the concentration of the compound in the chemostat device at time t, and the other values are as in step (c), (e) determining the relationship between the growth rate and the concentration of the compound by determining the time at which the growth rate reached zero and the compound concentration at that time, or by graphing growth rate and compound concentration on the same graph, or by graphing growth rate as a function of compound concentration, whereby the effect of said compound on said microorganism is determined.

* * * * *